US005633010A

United States Patent [19]
Chen

[11] Patent Number: 5,633,010
[45] Date of Patent: *May 27, 1997

[54] ADHESIVE COMPOSITIONS, WOUND DRESSINGS AND METHODS

[75] Inventor: Yen-Lane Chen, New Brighton, Minn.

[73] Assignee: Minnesota Mining and Manufacturing Company, St. Paul, Minn.

[*] Notice: The term of this patent shall not extend beyond the expiration date of Pat. No. 5,622,711.

[21] Appl. No.: 469,023

[22] Filed: Jun. 6, 1995

Related U.S. Application Data

[62] Division of Ser. No. 351,890, Dec. 8, 1994, which is a continuation of Ser. No. 956,616, Oct. 5, 1992, abandoned.

[51] Int. Cl.$^6$ ..................................................... A61F 13/02
[52] U.S. Cl. .......................... 424/448; 424/443; 424/445; 424/447; 424/449; 524/528
[58] Field of Search .............................. 424/445, 447, 424/448, 449, 443; 524/528

[56] References Cited

U.S. PATENT DOCUMENTS

| 2,927,868 | 1/1960 | Revoir | 117/76 |
|---|---|---|---|
| 3,339,546 | 9/1967 | Chen | 424/445 |
| 3,532,679 | 10/1970 | Steckler | 260/80.72 |
| 3,877,431 | 4/1975 | Kross | 128/283 |
| 3,972,328 | 8/1976 | Chen | 128/156 |
| 3,980,084 | 9/1976 | Kross | 128/283 |
| 4,078,568 | 3/1978 | Etes et al. | 128/283 |
| 4,152,231 | 5/1979 | St. Clair et al. | 204/159.17 |
| 4,166,051 | 8/1979 | Cilento et al. | 260/17.4 |
| 4,192,785 | 3/1980 | Chen et al. | 260/17.4 |
| 4,204,540 | 5/1980 | Cilento et al. | 128/283 |
| 4,231,369 | 11/1980 | Sorensen et al. | 128/283 |
| 4,421,822 | 12/1983 | Levens | 428/343 |
| 4,477,325 | 10/1984 | Osburn | 204/159.12 |
| 4,496,357 | 1/1985 | Osburn | 604/336 |
| 4,538,603 | 9/1985 | Pawelchak et al. | 128/156 |
| 4,539,256 | 9/1985 | Shipman | 428/315.5 |
| 4,551,490 | 11/1985 | Doyle et al. | 424/445 |
| 4,598,004 | 7/1986 | Heinecke | 428/40 |
| 4,728,442 | 3/1988 | Pawelchak et al. | 514/57 |
| 4,738,257 | 4/1988 | Meyer et al. | 424/443 |
| 4,738,259 | 4/1988 | Brown et al. | 128/136 |
| 4,768,503 | 9/1988 | Highgate et al. | 128/156 |
| 4,952,618 | 8/1990 | Olsen | 524/17 |
| 5,032,403 | 7/1991 | Sinnreich | 424/448 |
| 5,059,189 | 10/1991 | Cilento et al. | 604/307 |
| 5,066,728 | 11/1991 | Audett | 525/314 |
| 5,270,358 | 12/1993 | Asmus | 524/55 |
| 5,429,591 | 7/1995 | Yamamoto et al. | 602/54 |

FOREIGN PATENT DOCUMENTS

| 538658 | 8/1984 | Australia . |
|---|---|---|
| 1128681 | 7/1982 | Canada . |
| 0081907 | 6/1983 | European Pat. Off. . |
| 0249694 | 12/1987 | European Pat. Off. . |
| 0272149 | 6/1988 | European Pat. Off. . |
| 0343807 | 11/1989 | European Pat. Off. . |
| 91/19480 | 12/1991 | European Pat. Off. . |
| 2046764 | 4/1983 | United Kingdom . |
| 91/06290 | 5/1991 | WIPO . |
| 0272149 | 3/1992 | WIPO . |

OTHER PUBLICATIONS

K. Tsukada et al., "The pH Changes of Pressure Ulcers Related to the Healing Process of Wounds", 4,*WOUNDS:A Compendium of Clinical Research and Practice*, 16 (Jan.-Feb., 1992).

"Cellulose Derivatives, Ethers",*Encyclopedia of Chemical Technology* (Kirk–Othmer) 3rd Ed., vol. 5, 143–149.

Bovey, *Effects of High Energy Radiation on Polymers*, 43–45 (1958).

*Primary Examiner*—Raj Bawa
*Attorney, Agent, or Firm*—Gary L. Griswold; Walter N. Kirn; Paul W. Busse

[57] ABSTRACT

Hydrocolloid adhesive compositions are disclosed comprising a hydrophobic unsaturated aliphatic homopolymer, a compatible tackifier, and at least one hydrocolloid absorbent. The compositions have enhanced resistance to breakdown by body fluids, adjustable absorbency, improved adhesive and cohesive properties, as well as a reduced tendency to leave an adhesive residue after application. Also disclosed are wound dressings, ostomy or prosthesis adhesives, methods of using wound dressings, and methods for forming the hydrocolloid adhesive compositions.

17 Claims, 1 Drawing Sheet

ADHESIVE COMPOSITIONS, WOUND DRESSINGS AND METHODS

This is a division of application No. 08/351,890, filed Dec. 8, 1994, which is a continuation of application No. 07/956,616, filed Oct. 5, 1992, now abandoned.

FIELD OF THE INVENTION

This invention relates to hydrocolloid adhesive compositions having a variety of medical uses, particularly in the field of wound dressings, ostomy care, and prosthesis application. In addition, this invention also relates to wound dressings, a method of using such wound dressings, ostomy and/or prosthesis adhesives, and to methods of forming a hydrocolloid adhesive composition.

BACKGROUND OF THE INVENTION

Hydrocolloid adhesive compositions, as well as wound dressings and ostomy products formed from these adhesive compositions, have been known for many years. Typically, these compositions comprise a blend of a polymer matrix, such as a rubbery elastomer like polyisobutylene, in combination with one or more water-soluble or water-swellable hydrocolloids, such as a dry powdered mixture of pectin, gelatin and carboxymethylcellulose. When included in a wound dressing or ostomy seal, the adhesive composition is usually coated on at least one surface of a water-insoluble film. See e.g., U.S. Pat. Nos. 3,980,084, 3,877,431, 3,532,679, and 3,339,546, and European Patent Application No. 0343807. A commercially available example of a composition of this type is STOMADHESIVE™ (E. R. Squibb & Sons Inc., Princeton, N.J.), which is used as a skin barrier around stomas to prevent skin breakdown by the corrosive fluids discharged by the stoma.

A major problem with many conventional hydrocolloid adhesive compositions is their susceptibility to breakdown upon exposure to wound exudate and body fluids (i.e. their lack of structural integrity after being hydrated). When the compositions are used as skin barriers, e.g., around stomas, some absorption of fluid is desirable, but excessive swelling causes the composition to lose its moisture seal with the skin. Leakage occurs and the barrier must be replaced more often than is desirable.

Furthermore, when the adhesive compositions are used as wound dressings, the compositions tend to dissolve upon exposure to wound exudate and form a gel on the surface of the wound. When the dressing is removed, a residue remains on the wound requiring removal, typically by irrigation. When this breakdown occurs the dressings may also lift off the wound and allow leakage of wound exudate onto clothing and bedding.

Accordingly, a number of attempts have been made to improve the integrity of hydrocolloid adhesive compositions, and the resulting wound dressings and ostomy products.

U.S. Pat. No. 4,496,357 describes the incorporation of fumed silica into hydrocolloid compositions to control swelling.

U.S. Pat. No. 4,551,490 describes a hydrocolloid adhesive composition of a homogenous blend of mineral oil, one or more polyisobutylenes alone or in combination with an elastomer such as butyl rubber, styrene radial or block copolymers, water-soluble hydrocolloid gums, water-swellable cohesive strengthening agents, and a tackifier. Both the elastomer and water-swellable agents are said to add cohesive strength to the composition, while the styrene radial or block copolymers are said to provide extensibility and recovery from modular strains associated with hydration. See also, U.S. Pat. Nos. 4,204,540, 4,192,785, and 4,166,051.

U.S. Pat. No. 4,952,618 discloses a hydrocolloid adhesive composition formed from a rubbery elastomeric base having hydrocolloid particles, at least some of which are polycationic, dispersed therein. The composition is said to exhibit improved integrity attributable to the polycationic particles contained in the compositions, particularly when combined with anionic hydrocolloid particles, either alone, or further mixed with neutral hydrocolloid particles.

In a different approach, U.S. Pat. Nos. 4,538,603 and 4,728,442 disclose a granular wound packing that is covered with a separate occlusive dressing. In general, the occlusive dressing component can include a variety of hydrocolloid materials in combination with one or more pressure sensitive adhesive elastomers, such as polyisobutylene, and one or more thermoplastic elastomers, such as butyl rubber and styrene copolymers.

Another manner of addressing lack of structural integrity is to provide hydrocolloid adhesive compositions where one or more of the polymeric components are chemically or physically cross-linked. For example, U.S. Pat. No. 4,768,503 provides a adhesive composition of one or more chemically cross-linked hydrophilic polymers in combination with a support matrix of a high molecular weight hydrophobic polymer.

U.S. Pat. Nos. 4,477,325 and 4,738,257 describe incorporating into a hydrocolloid composition a mixture of a copolymer resin of ethylene and vinyl acetate (EVA). After mixing and molding, the composition is subjected to ionizing radiation to form cross-linked polymer networks of the EVA or EVA with another cross-linkable resin. The cross-linked matrix is said to provide controlled swelling.

In a similar vein, U.S. Pat. No. 4,231,369 and European Patent Publication No. 0272149 disclose various hydrocolloid materials dispersed within a physically cross-linked gel-like phase. In general, the gel-like phase is comprised of elastomeric materials, such as A-B-A block copolymers, as well as certain ethylene/propylene copolymers, that are said to be physically cross-linked due to phase separation and reformation of the materials after melt processing.

In general, the efforts to date at providing a high integrity hydrocolloid adhesive compositions, and associated wound dressings and ostomy barriers, have not proven to be very effective. Furthermore, even when such materials demonstrate improved integrity, such an improvement has typically been at the expense of a number of other desirable properties, such as absorption, good edge adhesion, shear holding power, cohesive strength, lack of adhesive residue, reduced adhesive cold-flow, increased conformability and elasticity, and decreased skin sensitivity.

SUMMARY OF THE INVENTION

In contrast to existing materials, the hydrocolloid adhesive compositions and associated wound dressings of the present invention exhibit consistently high wet integrity, and thus provide dressings that maintain their form and impart a minimum amount of hydrocolloid residue, if any, to a wound and the surrounding skin. In addition, the adhesive compositions can be formulated to provide a wide range of absorbency, including high absorbency for wound dressings, and low absorbency for ostomy and prosthesis adhesives, and still maintain optimal wet integrity. Furthermore, these adhesive compositions and dressings provide a number of other advantages, including good edge adhesion, high shear holding power, lack of adhesive residue, reduced adhesive cold-flow, good adhesion to skin, and good cohesive strength.

In particular the present invention provides a pressure sensitive adhesive composition comprising a hydrophobic unsaturated aliphatic homopolymer cross-linked by a dose of radiation, a compatible tackifier, and at least one hydrocolloid absorbent. Preferably, the pressure sensitive adhesive composition exhibits a wet integrity of at least about eighty percent.

The present invention also provides a wound dressing comprising the above-described pressure sensitive adhesive composition coated on at least a portion of one major surface of a moisture vapor permeable backing. Furthermore, the present invention provides a method of treating a wound comprising applying to the wound the above-described pressure-sensitive adhesive composition.

In another aspect, the present invention provides an ostomy or prosthesis adhesive comprising the above-described pressure sensitive adhesive composition having an absorbency value of less than about fifty percent at twenty-four hours. In addition, the ostomy or prosthesis adhesive also preferably exhibits a shear hold value of at least about 500 minutes/500 g.

In yet another aspect, the present invention provides a method of forming a pressure sensitive adhesive composition comprising compounding a mixture of a hydrophobic unsaturated aliphatic homopolymer, a compatible tackifier, and at least one hydrocolloid absorbent to form a hydrocolloid adhesive mass, and irradiating the hydrocolloid adhesive mass with a dose of radiation of from about 5 kGy (0.5 Mrad) to about 200 kGy (20 Mrad).

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

The invention may be further illustrated by reference to the accompanying Drawings wherein.

DETAILED DESCRIPTION OF EMBODIMENTS OF THE INVENTION

Adhesive Compositions

Figure 1:
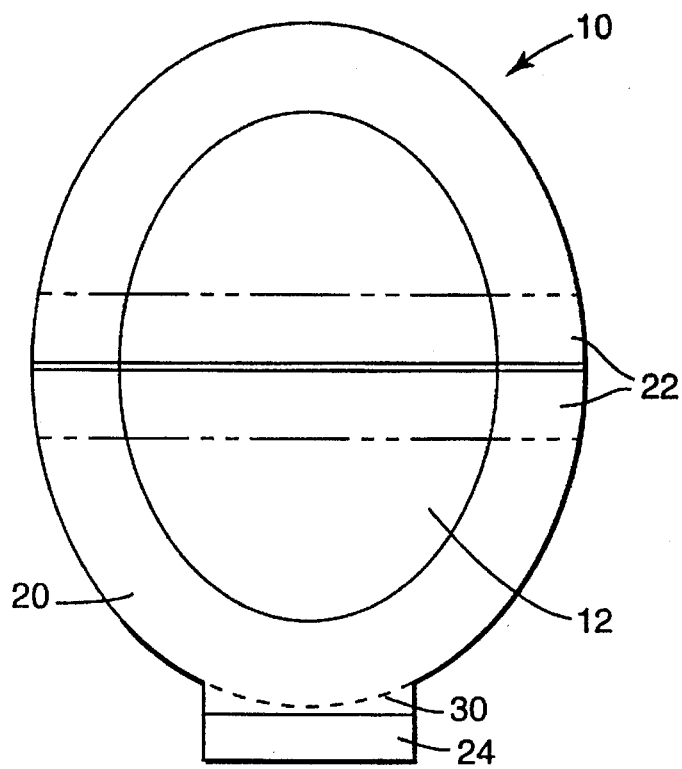
FIG. 1 is a top view of a wound dressing incorporating the hydrocolloid adhesive composition of the present invention.

The hydrocolloid adhesive compositions of the present invention comprise a blend of at least three basic ingredients, viz., the hydrophobic unsaturated aliphatic homopolymer, a compatible tackifier, and at least one hydrocolloid absorbent. This mixture of ingredients is exposed to a dose of ionizing radiation which chemically cross-links the hydrophobic unsaturated aliphatic homopolymer component, thereby yielding the high integrity adhesive compositions of the present invention. While it is preferable to irradiate the ingredients after mixing and formation into a desired shape (e.g. an adhesive sheet), it is possible to irradiate the ingredients prior to mixing and/or formation. However, in such an instance, the complete mixing of the ingredients may be impeded, and the resulting mixture may still need to exposed to a further dose of radiation to deliver the high integrity adhesive compositions of the present invention.

The hydrophobic unsaturated aliphatic homopolymer can comprise either a straight-chain unsaturated aliphatic homopolymer, a branched unsaturated aliphatic homopolymer, or a combination thereof. In addition, the hydrophobic unsaturated aliphatic homopolymer can be substituted along its polymer chain with another moiety, such as chlorine, fluorine, or a lower alkyl, and still be considered to fall within the scope of the present invention. However, substitution of other monomers within the polymer chain of the homopolymer (e.g., random, block, and sequential copolymers) is not considered to be within the present invention.

As used herein, a "hydrophobic unsaturated aliphatic homopolymer" refers to organic homopolymers, typically olefin homopolymers, that are substantially water insoluble, and which exhibit a significant degree of unsaturated double bonds in the homopolymer chain and/or branched side chains. While potentially any degree of unsaturation may serve to form the adhesive compositions of the present invention, the hydrophobic unsaturated aliphatic homopolymer preferably exhibits at least about fifty mole percent (50%) unsaturation, and more preferably at least about ninety mole percent (90%) unsaturation. In an especially preferred embodiment, the hydrophobic unsaturated aliphatic homopolymer exhibits virtually one hundred mole percent (100%) unsaturation, i.e. essentially 100% unsaturated double bonds per monomer unit of the homopolymer.

Preferably, the hydrophobic unsaturated aliphatic homopolymer comprises an elastomeric homopolymer. Nonlimiting examples of suitable elastomeric homopolymers include polyisoprene, polybutadiene, and combinations thereof, with polyisoprene being particularly preferred. Polyisoprene is commercially available from a number of sources, including Goodyear Chemical Co., Akron, Ohio, under the NATSYN™ trademark, including Natsyn resin Nos. 2200, 2205, and 2210.

The hydrophobic unsaturated aliphatic homopolymer preferably comprises from about 20 percent to about 50 percent, by weight of the hydrocolloid adhesive compositions of the present invention. For wound dressing applications, it is desirable to limit the amount of hydrophobic unsaturated aliphatic homopolymer present, in order to maximize the level of hydrocolloid, thereby achieving maximum fluid absorbency. Thus, when forming wound dressings, from about 25 weight percent to about 35 weight percent of the hydrophobic unsaturated aliphatic homopolymer is employed. Conversely, when formulating an adhesive composition for an ostomy skin barrier and/or application of prostheses, maximum hold and minimal absorbency in desired. Thus, adhesive composition of the present invention that are formulated for ostomy and/or prosthesis attachment preferably comprise from about 35 weight percent to about 45 weight percent of hydrophobic unsaturated aliphatic homopolymer.

The compatible tackifier can comprise either an elastomeric tackifier, such as polyisobutylene, or a nonelastomeric tackifier, including synthetic polyterpene tackifiers, such as WINGTACK™ brand tackifiers (e.g., Wingtack 10, Wingtack 86, Wingtack 95, Wingtack Plus, and Wingtack Extra) available from Goodyear Chemical Co., Akron, Ohio, or a combination of elastomeric and non-elastomeric tackifiers. As used herein, a "compatible tackifier" refers to a tackifier that is miscible with the hydrophobic unsaturated aliphatic homopolymer, such that when the these components are mixed they form a homogeneous phase.

Preferably, the compatible tackifier comprises low molecular weight polyisobutylene (viscosity average molecular weight of from about 20,000 to 70,000, preferably from about 40,000 to about 65,000). Suitable low molecular weight polyisobutylene tackifiers are available from Exxon Chemical Company under the tradenames Vistanex LMand Vistanex L-100, respectively, and include Vistanex LM-MS (viscosity average molecular weight=44,000), Vistanex LM-MH (viscosity average molecular weight=53,000), and Vistanex LM-H (viscosity average molecular weight=63,000).

The compatible tackifier preferably comprises from about 20 weight percent to about 60 weight percent, and more preferably from about 30 weight percent to about 50 weight percent of the hydrocolloid adhesive compositions of the present invention.

The hydrocolloid absorbent can comprise a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X-link CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B. F. Goodrich, Brecksville, Ohio), or a combination thereof. Preferably, the hydrocolloid absorbent component comprises from about 5 percent to about 60 percent by weight of the adhesive composition. When preparing an adhesive composition for use in a wound dressing the hydrocolloid absorbent preferably comprises from about 20 percent to about 40 percent by weight of the composition, while for an ostomy or prosthesis adhesive the hydrocolloid absorbent preferably comprises from about 5 percent to about 20 percent by weight of the total adhesive composition.

The particular selection of the hydrocolloid absorbents to be used in any one adhesive formulation will depend upon the intended use for that formulation. For example, in preparing an adhesive composition for use with a wound dressing, maximum absorbency without a loss of wet integrity is desired. Thus, a major portion of the hydrocolloid absorbent should comprise natural hydrocolloids that are water soluble, and provide maximum absorbency. In addition, cross-linked semi-synthetic and synthetic hydrocolloids, which are water swellable, but water insoluble, may also be included in the composition to serve as a filler, and/or to help regulate the swelling of adhesive composition. Conversely, when formulating ostomy and/or prosthesis adhesives, minimal, if any absorbency, is desired. In such an instance, the cross-linked semi-synthetic and synthetic hydrocolloids would comprise the majority, if not all, of the hydrocolloid absorbent in the adhesive composition.

Thus, the absorbency of the hydrocolloid adhesive compositions of the present invention can be adjusted based on the particular need. In general, for ostomy and/or prosthesis adhesives the composition will preferably exhibit an absorbency value of less than about 50 percent, and more preferably less than about 20 percent after twenty-four hours of exposure to aqueous fluids. On the other hand, when formulating an adhesive composition for use in a wound dressing the composition will preferably exhibit an absorbency of at least 50 percent, and more preferably an absorbency of from about 100 percent to about 500 percent after twenty-four hours of exposure to aqueous fluids.

The use of cross-linked polyacrylic acid (PAA) as a hydrocolloid absorbent may provide additional advantages to adhesive compositions according to the present invention. Specifically, the acidic nature of PAA lowers the overall acidity of the adhesive compositions of the present invention from a pH of about 7 to a pH of about 5. When such a composition is employed in a wound dressing, the pH of the wound exudate will likewise be lowered. This in turn may lead to promotion of more rapid healing of the wound. See e.g., K. Tsukada et al., "The pH Changes of Pressure Ulcers Related to the Healing Process of Wounds", 4, *WOUNDS: A Compendium of Clinical Research and Practice*, 16 (Jan.-Feb., 1992). In addition, the use of PAA has also been observed to reduce the cold-flow of the adhesive layer of wound dressings formed from the adhesive compositions of the present invention.

The adhesive compositions of the present invention may also optionally contain a plasticizer component at from about 0.5 percent to about 10 percent by weight of the total adhesive composition. Preferably, the plasticizer comprises mineral oil (Spectrum Corp., Gardena, Calif.).

Compositions of the present invention may also contain minor amounts of other ingredients such as antioxidants, deodorants, perfumes, antimicrobials and other pharmacologically active agents as is well known in the art. Furthermore, additional elastomers, including polypropylene-polyethylene copolymers such as EPSYN™ resins available from Copolymer Rubber and Chemical Corp., Baton Rouge, La., can also be included in the compositions of the present invention.

Compositions of the invention are made by compounding the hydrophobic unsaturated aliphatic homopolymer and compatible tackifier with a heavy duty mixer until a homogeneous blend is obtained. Small portions of a dry-blended premix of one or more hydrocolloid absorbents are added and milling continued until a homogeneous dispersion of the absorbents in the adhesive phase is obtained. The blended adhesive mass is then molded into sheets for further conversion into wound dressings or formed into shapes such as strips, rings, etc., by any number of means commonly used for converting plastics and elastomers into shapes such as compression or injection molding. In addition, the blended adhesive mass can also be fed into a heated single- or dual-screw extruder and coated from a standard extrusion die to form adhesive sheets capable of being converted into appropriately shaped materials.

After formation, the adhesive compositions of the present invention are irradiated with a dose of ionizing radiation at from about 5 kGy (0.5 Mrad) to about 200 kGy (20 Mrad), more preferably at a dose of from about 25 kGy (2.5 Mrad) to about 50 kGy (5 Mrad). Both E-beam and gamma irradiation can serve as the ionizing radiation source used to irradiate the adhesive compositions of the present invention, and thereby chemically cross-link the hydrophobic unsaturated aliphatic homopolymer component of the adhesive composition. It is this cross-linking of the hydrophobic unsaturated aliphatic homopolymer component that results in the consistently high wet integrity displayed by the adhesive compositions of the present invention. In addition, the application of ionizing radiation can also be used to sterilize the adhesive compositions and/or wound dressings of the present invention.

The degree of cross-linking in the adhesive compositions of the present invention can be gauged by measuring the percent gel content of the hydrophobic unsaturated aliphatic homopolymer component after being exposed to a pre-determined dose of ionizing radiation. Specifically, the irradiated hydrophobic unsaturated aliphatic homopolymer is placed in a nonpolar organic solvent, such as hexane, heptane, or toluene, that is normally capable of dissolving the homopolymer. Any cross-linked homopolymer will form a gel in the solvent, while non-cross-linked homopolymer will dissolve. The remaining gelled homopolymer is removed from the solvent, washed, dried, weighed, and expressed as a percent by weight of the original irradiated material. This gel percent measurement can then be used to gauge the amount of cross-linking, and thereby the specific dose of radiation required to yield the high wet integrity compositions of the present invention. Accordingly, the hydrophobic unsaturated aliphatic homopolymer component of the compositions of the present invention should preferably exhibit at least 50 percent gel content, and more preferably at least 70 percent gel content. The specific dosage of radiation required to reach this level of gel content will depend upon the particular hydrophobic unsaturated aliphatic homopolymer chosen for inclusion in the compositions of the present invention.

Wound Dressings

Figure 2:
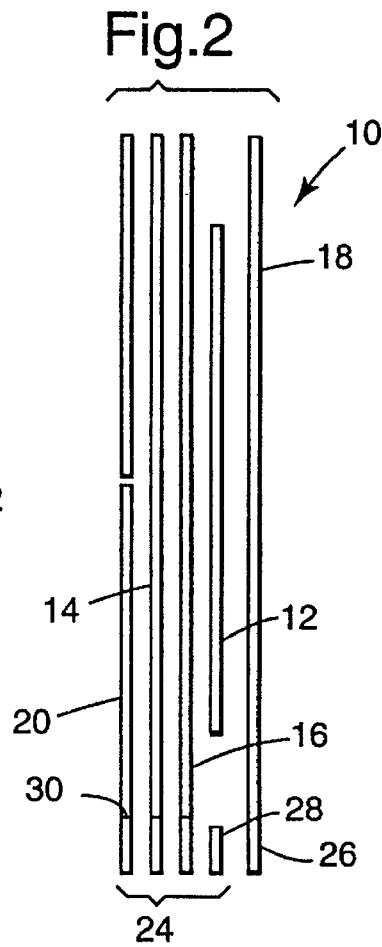
FIG. 2 is an exploded side view of the dressing of FIG. 1.

Referring now to FIGS. 1 and 2, wound dressing 10 comprises an oval-shaped sheet 12 of the hydrocolloid adhesive composition of the present invention. Laminated to the top side (side facing away from the skin when the dressing is in use) is a slightly larger oval-shaped transparent film backing 14. An intermediate layer 16 of a conventional pressure-sensitive skin adhesive is used to facilitate lamination. The peripheral portion of the film backing 14 and adhesive layer 16 extends beyond the hydrocolloid sheet 12 to assist in adhering the hydrocolloid sheet 12 to the skin. A conventional release liner 18 is used to protect the exposed surface of the hydrocolloid sheet 12 and the exposed portion of the adhesive layer 16 prior to use. Delivery sheet 20 is attached to the top side of film backing 14 to prevent wrinkling and curling of the edges of backing 14 and adhesive layer 16 after removal of release liner 18. Delivery sheet 20 is divided into two sections of approximately equal size and heat-sealed to the top side of film backing 14. Both sections have a non-heat-sealed edge 22 at the center of the dressing to form handles which facilitate grasping and removal of the delivery sheet. Delivery sheet 20 supports the exposed periphery of backing 14 and adhesive layer 16 during application of the dressing to the patient. Once the dressing is in place on the skin, delivery sheet 20 is removed.

Separation of the release liner 18 from the hydrocolloid sheet 12 and adhesive layer 16 of the dressing 10 is facilitated by two tabs 24 and 26. Tab 24 comprises aligned rectangularly-shaped extensions of each of the delivery sheet 20, film backing 14 and adhesive layer 16, and further comprises a stiffening member 28 adhered to the adhesive layer 16 to facilitate separation of the tab members from each other. The second tab 26 is aligned with tab 24 and comprises a rectangularly-shaped extension of release liner 18. A perforation line 30 separates tab 24 from the main oval section of the dressing. Tab 24 provides an area for the person applying the dressing to hold onto without touching or otherwise contaminating the adhesive 14 and hydrocolloid sheet 12 in the main oval portion of the dressing. After the dressing is in place on the patient, tab 24 can be separated from the main oval portion of the dressing along perforation line 30. In a particularly preferred embodiment, the dressing 10 comprises a second opposing tab (not shown) on the opposite side of the dressing 10 from tab 24 to further facilitate the holding and application of the dressing 10 without contamination of the hydrocolloid sheet 12 or wound site.

The dressing illustrated in FIGS. 1 and 2 is the presently preferred embodiment of the invention. The oval shape reduces dressing size and minimizes edge lift.

The film backing 14 is preferably a highly moisture vapor permeable film of, for example, porous polyethylene such as that disclosed in U.S. Pat. No. 4,539,256 or polyurethane such as that described in U.S. Pat. Nos. 3,645,535 or 4,598,004. Moisture vapor permeable films of this type allow the wound exudate to evaporate through the dressing and reduce the pooling of exudate under the dressing. The moisture vapor transmission rate of the backing is preferably at least 500 grams/square meter/24 hours when measured at 40° C. and 80 percent humidity differential. Film backing 14 is preferably about 0.026 mm (1 mil) thick.

In a preferred aspect, the film backing 14 further comprises a release surface (not shown), such as a low adhesion backsize, coated on the surface of the backing 14 opposite from the hydrocolloid sheet 12 and adhesive layer 16. A commercially available example of a suitable backing with a low adhesion backsize coating for use with the present invention is TEGADERM™ No. 1620 dressing (3M Company, St. Paul, Minn.). By using a film backing 14 containing a release surface, the wound dressing 10 can have other tapes applied over the dressing after its application to a patient. This ability to tape-over the wound dressing allows the dressing to serve as an attachment site or platform for other medical devices. After a period of time, these tapes can be easily removed without disturbing or otherwise having to also remove the wound dressing 10, and thereby expose the wound to further contamination.

Adhesive layer 16 is also preferably moisture vapor permeable so as not to detract significantly from the moisture vapor permeability of the film backing 14. Suitable medical adhesives of this type, such as the copolymer acrylate adhesive and polyvinyl ether adhesive described in U.S. Pat. Nos. 4,598,004 and 3,645,535, respectively, are well known. The adhesive is preferably about 0.026–0.075 mm (1–3 mils) thick.

Delivery sheet 22 is preferably a polyester-film with a polyethylene-ethylvinyl acetate heat seal coating available commercially from 3M, under the trademark Scotchpack 1220.

Hydrocolloid sheet 12 preferably has the composition of Example 28 below and has a thickness between 1.0–1.75 mm (40–70 mils).

Figure 3:
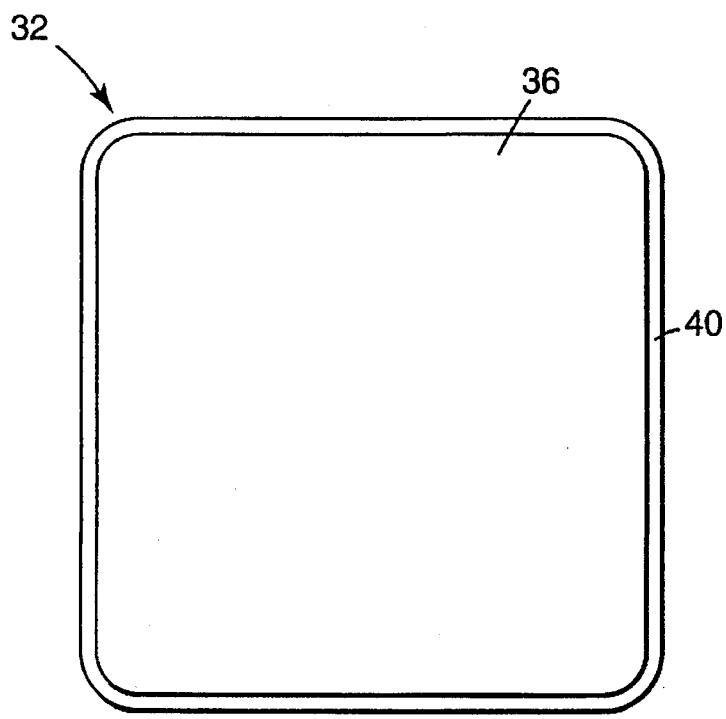
FIG. 3 is a top view of an alternative embodiment of a wound dressing incorporating the hydrocolloid adhesive composition of the present invention.
Figure 4:
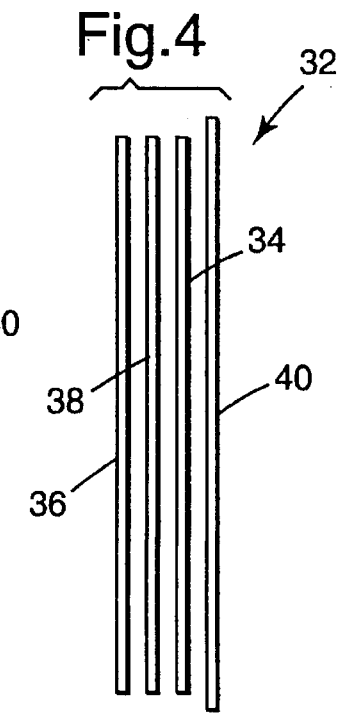
FIG. 4 is an exploded side view of the dressing of FIG. 3.

The dressing of FIGS. 3 and 4 represents an alternative embodiment of a wound dressing 32 which incorporates the hydrocolloid adhesive composition of the present invention. Dressing 32 comprises a square sheet 34 of the hydrocolloid adhesive composition. A square film backing 36 of the same dimensions as the hydrocolloid sheet is laminated to the top surface (facing away from the skin) of the hydrocolloid sheet by adhesive layer 38. Release liner 40 covers the exposed surface of hydrocolloid sheet 34 and extends outwardly from the hydrocolloid sheet on all sides to facilitate grasping of the liner 40 and removal thereof prior to application of the dressing to the wound. The materials which can be used to form film backing 34 and adhesive layer 38 are essentially the same as those discussed above in connection with the embodiment of FIGS. 1 and 2. The dressing of FIG. 3 is cheaper to manufacture than the dressing of FIG. 1 and is also easier to cut to the dimensions of the wound.

The hydrocolloid adhesive compositions and dressings of the present invention exhibit increased integrity over other commercially available compositions. In addition, the compositions and dressings of the invention also exhibit adjustable absorbency, high shear holding power, good adhesion to skin, good cohesive strength, good edge adhesion, reduced adhesive cold-flow, and reduced adhesive residues. The integrity, absorbency, 90° peel adhesion, skin adhesion, edge lift, skin adhesive residue, and shear hold force of the compositions of the present invention were determined according to the following test procedures.

Integrity Test

Preweighed ($W_i$) test samples of a dressing (each a 5 cm disc) are placed in an 6 oz (180 ml) bottle containing 30 ml of phosphate buffered saline solution (pH 7.2) (Sigma Chemical Company, St. Louis, Mo.). The bottles are capped and agitated on a shaker (Eberbach Co., Ann Arbor, Mich.) at low speed for a period of 24 hours. Remaining test samples are removed, transferred to a metal pan, and dried in a forced-air oven maintained at 65° C. until dry (typically overnight; i.e. 12–16 hours) and weighed ($W_f$).

The Integrity Value of the sample is calculated using the following equation:

$$\text{Integrity Value} = \frac{W_f}{W_i} \times 100$$

Compositions of this invention exhibit an Integrity Value of at least about 80 percent and preferably at least about 90 percent. Specific integrity values are reported in Tables 2, 4, and 7 below.

Absorption Test

Preweighed($W_i$) test samples (each a 5 cm disc) of a dressing are placed in an 6 oz (180 ml) bottle containing 30 ml of phosphate buffered saline solution (pH 7.2) (Sigma Chemical Company). The bottles are capped and allowed to stand without agitation. Samples are removed intermittently at fixed intervals, blotted dry, and weighed, including a final removal after 24 hours of exposure, and a final weighing ($W_t$). The Absorbency Value is calculated using the following formula:

$$\text{Absorbency Value} = \frac{W_t - W_i}{W_i} \times 100$$

Absorbency data is reported for the dressing compositions listed in Tables 2, 4 and 7 below. The absorbency of the compositions of the present invention can be adjusted depending upon the intended use (e.g., ostomy vs. wound dressings). When a wound dressing is desired, the compositions of the present invention exhibit a twenty-four hour absorbency value of at least about fifty percent (50%), and preferably from about one hundred percent (100%) to about five hundred percent (500%). When an ostomy or prosthesis adhesive composition is desired, the absorbency of the composition should be as low as possible, preferably below about fifty percent (50%), and even more preferably below about twenty percent (20%) after 24 hours of exposure to aqueous fluids.

90 Degree Peel Adhesion

Peel adhesion for wound dressings formed from the adhesive compositions of the present invention was measured using a 90° rotary peel adhesion test on an Instron testing machine (Model No. 1122; Instron Corp., Canton, Mass.). A 2.5 cm wide polyester adhesive tape (No. 1280 circuit plating tape; 3M Company) was adhered to a rotatable metal wheel which was mounted on the lower jaw of the Instron machine. The sample wound dressings were die cut into 1 cm×6 cm strips, each of which was placed on the tape covered wheel with the backing facing the operator. The strip was then pressed and adhered to the polyester tape substrate with a 2 kg rubber roller. Prior to testing, one end of the sample strip was lifted away from the substrate to form a tab, which was clamped onto the upper jaw of the Instron machine. The strip was then slowly peeled off the polyester tape substrate at a 90° angle and a crosshead speed of 10 mm/min. The peel force was recorded in grams per cm on a chart recorder.

Skin Adhesion

Adhesion to skin was determined on human volunteers utilizing wound dressings formed from the adhesive compositions of the present invention. The laminate dressings were cut into 2.5 cm×7.6 cm strips which were applied to the backs (left side=dry; right side=wet) of a selected number of volunteers (i.e. an equal number of randomly selected men and women). During application and removal of the test strips, the volunteers were lying on procedure tables in prone positions with arms at their sides and heads turned to one side. For each individual, two or three strips of the test material were applied on each of the sides of the spinal column and positioned such that the length of each strip was at a right angle to the spinal column. The strips were applied without tension or pulling of the skin and there was at least 0.3 cm to 1 cm space between each strip. After all strips were in place, a 2 kg rubber roller according to the specifications found in the 7th Edition of the Pressure-Sensitive Tape Council Brochure (1976), was rolled along the length of each strip, once in each direction, at a travel speed of about 7.6 cm per second, to assure even pressure application of each strip. When rolling the strip, no manual pressure was applied to the roller.

To determine the adhesive value, each strip was removed using a conventional adhesion tester having a 11.4 kg test line and a 2.5 cm clip attached to the test line. The clip was attached to the edge of the strip which is farthest from the spinal cord, the clip being attached by manually lifting about 1 cm of that edge of the strip and attaching the clip thereto. This orientation permitted the strip to be removed towards the spine so that pull was with the direction of fine hair growth on the back. This was facilitated by positioning the adhesion tester opposite the side of the individual's back from which the strip was to be removed. The adhesion tester was aligned with, and was at the same height as, the strip to be removed. An example of a suitable adhesion tester for use in this test comprises a conventional motor driven screw with moving carriage and a transducer. Connection to the transducer was a load cell accessory. Removal force placed on the transducer resulted in a signal change which was passed through a readout meter to a strip chart recorder.

Edge Lift and Skin Adhesive Residue

The amount of adhesive residue remaining on the skin of volunteers after a defined amount of time was measured after removal of the wound dressing sample strips in the skin adhesion test described above. In addition, prior to the removal of the sample strips the amount to which the edge or edges of the sample strips had lifted off the skin was quantified. Both edge lift and adhesive residue was subjectively measured by an expert familiar with adhesive tape performance, including edge lift and residue evaluation. The evaluator judged the percent of area of the edge(s) of the sample strips that had lifted away from the skin, as well as the percent area of underlying skin covered by any adhesive residue. Both of these determinations were graded on a scale of 0–5 as, 0=no lift or residue (i.e. 0%); 1=edge lift; 2=1% to 25% residue/lift; 3=26% to 50% residue/lift; 4=51% to 75% residue/lift; and 5=76% to 100% residue/lift.

Shear Hold

The test is a modification of ASTM D3654. 2.5 cm×15.2 cm test strips are adhered using light finger pressure to 7.6×7.6 cm panels of bright annealed stainless steel which have been prewashed once with diacetone alcohol and thrice with heptane. A 5.1 cm×14 cm auxiliary panel is placed flush with the testing edge of the test panel. The test strip is covered with a 2.54 cm×15.2 cm strip of polyethylene terephthalate film and rolled twice in each direction with a 2 kg roller at a rate of 30.5 cm per minute. The film was removed, then the auxiliary panel is carefully removed from the end of the tape. The tape end (about 7.6 cm) is folded back squarely over the center of an adapter hook, with the doubled portion being at least 2.5 cm long. The adhering length of the test strip is cut to exactly 2.5 cm in length. The test panel is placed in a stand holding both it and the adapter hook in a vertical position. A 500 g weight is hung on the adapter hook at a time designated as zero, and the time until the weight and test strip fall is measured. The shear holding power is expressed as units of time per 500 g.

The invention will be further illustrated by reference to the following non-limiting Examples. All parts and percentages are expressed as parts by weight unless otherwise indicated.

Examples 1–13, and Comparative Examples 14–26

Wound dressings incorporating the hydrocolloid adhesive compositions of the invention, as identified in Tables 1, 5 and 7 below, were made according to the same general procedure.

The adhesive phase of the dressing was prepared by compounding a mixture of a combination of dry solids consisting of a cross-linked polyacrylic acid (PAA) (CARBAPOL™ 974P; B. F. Goodrich, Brecksville, Ohio), sodium carboxymethylcellulose (CMC) (Aqualon Corp., Wilmington, Del.) and cross-linked sodium carboxymethylcellulose (X-link CMC) (Ac-Di-Sol; FMC Corporation, Philadelphia, Pa.) with a rubber blend of low molecular weight polyisobutylene (PIB) (LM-MH; Exxon Corp., Baton Rouge, La.) and polyisoprene (Natsyn 2210; Goodyear Chemical Co., Akron, Ohio). In addition, in some of the samples, mineral oil (Spectrum Corp., Gardena, Calif.) was also blended into the compounded mixture. The compounding was performed on a conventional two-roll rubber mill (Ferrel-Birmingham Co., Ansonia, Conn.), with the dry solids being gradually incorporated into the rubber blend as the mixture was passed repeatedly through the cold-water-chilled rollers during the milling process (typically 7–10 minutes). Entrapped air was removed from the compounded mixture by applying a vacuum of 762 mm of mercury. The blended hydrocolloid adhesive mass was then removed from the rubber mill and formed into flat adhesive sheets of about 10 cm by 10 cm and 0.64 mm thick, by compressing the mass in a Carver Laboratory Press (Fred S. Carver Inc., Menomonie, Wis.) maintained at approximately 65° C. and 110 Mega Pascals (MPa) between two sheets of silicone release paper (Daubert Coated Products, Dipon, Ill.). The release paper was removed from one side of the adhesive sheet, and the adhesive sheet was laminated to a polyurethane backing film coated with an acrylate adhesive copolymer (e.g., TEGADERM™ transparent dressing; 3M Company, St. Paul, Minn.). The resulting laminate structures were then die cut into the desired dressing shapes, and were then cross-linked and sterilized with gamma radiation at a dose of approximately 30–50 kGy (3–5 Mrads).

The dressings for Comparative Examples 14–26 were made using the same formulations and procedures of Examples 1–13, except that the final dressings were not irradiated by a dose of gamma radiation prior to testing.

The dressings were clear enough to read through with standard type on 8.5 by 11 inch paper (21.6 cm by 27.9 cm). The specific compositions of each of the Example and Comparative Example wound dressings is shown in Table 1. Absorbency, wet integrity, dry cohesive strength, and ninety degree peel adhesion for each of the Example and Comparative Example wound dressings is shown in Table 2.

TABLE 1

Specific composition of Example wound dressings 1–13 and Comparative Example wound dressings 14–26 (PIB = polyisobutylene, CMC = carboxymethylcellulose, PAA = polyacrylic acid, X-link CMC = cross-linked carboxymethylcellulose, and Min. Oil = mineral oil).

| Ex./ CEx. | LM-MH (PIB) | Polyisoprene | CMC | CARBOPOL (PAA) | X-link CMC | Min. Oil |
|---|---|---|---|---|---|---|
| 1/14 | 57.5 | 20 | 10 | 5 | 7.5 | 0 |
| 2/15 | 45 | 27.5 | 12.5 | 7 | 6 | 2 |
| 3/16 | 42.5 | 30 | 10 | 12.5 | 5 | 0 |
| 4/17 | 37.5 | 20 | 20 | 12.5 | 10 | 0 |
| 5/18 | 47.5 | 20 | 10 | 15 | 5 | 2.5 |
| 6/19 | 30 | 37.5 | 10 | 12.5 | 7.5 | 2.5 |
| 7/20 | 39 | 21.5 | 14.5 | 13 | 9 | 3 |
| 8/21 | 32.5 | 20 | 20 | 15 | 10 | 2.5 |
| 9/22 | 42.5 | 20 | 10 | 15 | 7.5 | 5 |
| 10/23 | 30 | 32.5 | 10 | 14.5 | 8.5 | 4.5 |
| 11/24 | 30 | 35 | 20 | 10 | 5 | 0 |
| 12/25 | 45 | 30 | 10 | 5 | 7.5 | 2.5 |
| 13/26 | 35 | 30 | 20 | 5 | 5 | 5 |

TABLE 2

Absorbency, wet integrity, dry cohesive strength, and ninety-degree peel adhesion for Example wound dressings 1–13 and Comparative Example wound dressings 14–26.

| Ex. No./ Comp. Ex. No | Absorb. (%)@ | Wet Integrity (%) | Dry Cohesive Strength (Pass–Fail) | 90° Peel Adhesion (g/cm) |
|---|---|---|---|---|
| 1/14 | 22/370 | 98/0 | Pass/Fail | 327/* |
| 2/15 | 90/280 | 95/0 | Pass/Pass | 254/193 |
| 3/16 | 49/210 | 99/99 | Pass/Fail | 158/* |
| 4/17 | 240/660 | 98/0 | Pass/Fail | 263/* |
| 5/18 | 221/410 | 95/91 | Pass/Fail | 388/* |
| 6/19 | 16/210 | 100/100 | Pass/Fail | 064/* |
| 7/20 | 274/520 | 94/0 | Pass/Fail | 250/* |
| 8/21 | 372/740 | 80/20 | Pass/Fail | 300/* |
| 9/22 | 282/456 | 93/93 | Pass/Fail | 270/* |
| 10/23 | 14/340 | 98/0 | Pass/Fail | 260/* |
| 11/24 | 42/130 | 96/0 | Pass/Fail | 122/* |
| 12/25 | 13/130 | 100/96 | Pass/Fail | 229/* |
| 13/26 | 63/540 | 93/0 | Pass/Fail | 250/* |

@absorbency values for Comparative Example dressings Nos. 14–26 were determined after 21 hours versus the 27 hours for Example dressings 1–13
*indicates cohesive failure of the tested dressing The data of Tables 1 and 2 show that the Example wound dressings 1–13 all exhibit a wet integrity value above 80%, and display varying absorbency values which can be adjusted based upon the intended use. Further, the Example wound dressings all maintain dry cohesive strength (i.e. Pass) as shown by the ninety-degree peel adhesion values obtained for these Example materials. A sample material is considered to have sufficient dry cohesive strength to "Pass" the requirements of the compositions of the present invention when the tested sample fails adhesively during peel adhesion testing, i.e. the sample dressing pulls away from the substrate substantially intact. In contrast, a sample material "Fails" to have sufficient dry cohesive strength when the adhesive layer breaks apart and/or delaminates from the backing during peel adhesion testing, leaving a significant portion of the adhesive composition adhered to the testing substrate.

In comparison to Example dressings 1–13, non-irradiated Comparative Example wound dressings 14–26 either display unacceptable wet integrity and/or fail to maintain cohesive strength when tested for peel adhesion. For example, while the wound dressing of Comparative Example No. 15 is able to maintain cohesive strength, and thereby register a peel adhesion value of 193 g/cm, it has zero wet integrity. Furthermore, the wound dressings of Comparative Examples 16, 20 and 23, maintain wet integrity, but fail cohesively when subjected to a peel adhesion test. Thus, these comparative materials would disintegrate or fail to remain adhered when applied to an exuding wound and/or would leave excessive adhesive residue both within the wound and on the surrounding skin when removed.

Examples 27–29

The adhesive phase of Example dressings 27–29 was formed as follows. A combination of dry solids consisting of sodium carboxymethylcellulose (CMC) (Aqualon Corp.) and crosslinked sodium carboxymethylcellulose (X-link CMC)(Ac-Di-Sol; FMC Corporation) was combined with low molecular weight polyisobutylene (PIB) (LM-MH; Exxon Corp.) and polyisoprene (Natsyn 2210; Goodyear Chemical Co.) in a conventional kneader-extruder (Ross-AMK Corp.; Hauppauge, N.Y.) to form a hydrocolloid adhesive mass. The mass, a homogenous mixture of powder and rubber, was passed through a single-screw extruder (Crompton & Knowles, Co., Pawcatuck, Conn.) while gradually increasing the extrusion temperature along the length of the extruder from about 73° C. to about 121°–138° C., and maintaining a pressure of about 19.3 Mega Pascals (MPa). Thereafter, the heated mass was passed through an extrusion die onto a web containing a silicone release liner (Dauberr Coated Products), and was coated at a thickness of about 0.4 mm and a width of about 20 cm. The dressings were prepared by laminating die cut rectangles or squares of the adhesive coated release liner onto a polyurethane backing (Estane resin; 0.04 mm; B. F. Goodrich). Alternatively, the dressings were prepared by first laminating the adhesive to the same backing described above coated with an acrylate copolymer adhesive (isooctyl acrylate/ethyl acrylate/acrylic acid; 70:15:15 with 0.5% of an polyethylene oxide (PEOX) catalyst). Thereafter, the adhesive coated backings were converted to dressings on a conventional roller-convertor apparatus, and were then die cut and packaged in low moisture vapor transmissive (MVT) film of polyethylene/saran/polyethylene terephthalate (Phoenix Health Care Products, Milwaukee, Wis.). The packaged and unpackaged dressings were then cross-linked and sterilized with a dose of gamma radiation at from about 30 kGy (3 Mrad) to about 50 kGy (50 Mrad). The dressings were clear enough to read through on using standard type on 8 ½ by 11 inch (21.6 cm by 27.9 cm) paper. The specific composition of the Example wound dressings is shown in Table 3.

TABLE 3

Specific composition of Example wound dressings 27–29.

| Ex. No. | LM-MH (PIB) | Polyisoprene | CMC | X-link CMC |
|---|---|---|---|---|
| 27 | 35 | 31 | 20 | 14 |
| 28 | 37.5 | 30 | 20 | 12.5 |
| 29 | 37.5 | 27.5 | 20 | 15 |

In order to evaluate the adhesive characteristics of the hydrocolloid dressings of the invention, the three dressings of Examples 27–29 were evaluated in comparison with several commercially available products, including DUODERM EXTRA-THIN™ wound dressing (a product of Convatec; Squibb and Sons, Inc., Princeton, N.J.; believed to be a KRATON™-based composition under U.S. Pat. No. 4,551,490), TEGASORB™ wound dressing (a product of 3M Company, St. Paul, Minn.; a polyisobutylene-based composition under U.S. Pat. No. 4,952,618), RESTORE™ wound dressing (a product of Hollister, Inc., Libertyville, Ill.; believed to be an ethylene vinyl acetate (EVA)-based composition under U.S. Pat. Nos. 4,477,325 and 4,738,257), and COMFEEL™ wound dressing (a product of Coloplast International, Espergaerde, Denmark; believed to be a KRATON™-based composition under U.S. Pat. No. 4,231,369).

The sample compositions, percent absorbency, percent wet integrity, sample edge lift, skin adhesion (wet and dry), skin residue (wet and dry), and total number of samples remaining on the backs of volunteers at the end of the test period for Example dressings 27–29 and the above-identified comparative products is shown in Table 4. In performing the skin adhesion, skin residue, edge lift, and samples remaining tests, both the TEGASORB™ and RESTORE™ products were tested on 8 volunteers (4 men and 4 women) using 3 replicates of each sample, and only on dry backs. For all other samples tested, 10 volunteers (5 men and 5 women) were used. Two replicates of each sample were applied to these volunteers, with the left side of the back being used as the dry side, and right side, after being moistened with water, being used as the wet side for test purposes.

TABLE 4

Sample composition, percent absorbency, percent wet integrity, sample edge lift, skin adhesion (wet and dry), skin residue (wet and dry), and the total number of test samples remaining on the backs of volunteers at the end of the study ($T_o$ = time initial; $T_F$ = time final) for Example wound dressings 27–29, and TEGASORB ™, RESTORE ™, DUODERM EXTRA-THIN ™, and COMFEEL ™ wound dressings.

| Sample Composition | Absorbency@ (%) | Wet Integrity (%) | Sample Edge Lift $T_F$ | Skin Adhesion | | | | Skin Residue | | | | Test Samples Remaining at $T_F$ |
|---|---|---|---|---|---|---|---|---|---|---|---|---|
| | | | | Dry $T_o$ | Dry $T_F$ | Wet $T_o$ | Wet $T_F$ | Dry $T_o$ | Dry $T_F$ | Wet $T_o$ | Wet $T_F$ | |
| Example 27 | 270 | 85 | 1.2 | 61 | 53 | 44 | 72 | 0 | 1.5 | 0 | 1.4 | 37 of 40 |
| Example 28 | 301 | 87 | 1.2 | 49 | 41 | 42 | 64 | 0.04 | 1.3 | 0.1 | 1.3 | 38 of 40 |
| Example 29 | 299 | 84 | 1.2 | 52 | 48 | 38 | 70 | 0 | 1.4 | 0 | 1.3 | 39 of 40 |
| TEGASORB ™ | 421 | 57 | 1.1 | 169 | 80 | — | — | 0.8 | 2.7 | — | — | 24 of 24 |
| RESTORE ™ | 313 | 0 | 2.1 | 64 | 67 | — | — | 1.4 | 3.7 | — | — | 20 of 24 |
| DUODERM EXTRA-THIN ™ | 185 | 68 | 1.4 | 177 | 56 | 83 | 67 | 2.2 | 2.5 | 1.9 | 2.1 | 37 of 40* |
| COMFEEL ™ | 84 | 82 | 1.7 | 48 | 60 | — | 27 | 0.1 | 1.2 | — | 1.4 | 26 of 40 |

$T_F$ for Examples 27–29, COMFEEL ™, and DUODERM EXTRA-THIN ™ measured at 72 hours, and for TEGASORB ™, and RESTORE ™ at 96 hours.
@Absorbency for Examples 27–29, TEGASORB ™, and COMFEEL ™ measured at 27 hours, for DUODERM EXTRA-THIN ™ at 23.5 hours, and for RESTORE ™ at 25 hours.
*1 tape fell-off, 2 tapes failed cohesively.

With the exception of the COMFEEL™ dressing, none of the other commercially available products displays the wet integrity of the dressings of the present invention. Thus, these products may undergo significant deterioration and/or leave excessive hydrocolloid residue when exposed to exudative wounds. In particular, the RESTORE™ product displays a complete loss of integrity after 24 hours of exposure in a shaker jar.

The COMFEEL™ product displays a number of other disadvantages, including very low absorbency for a wound dressing, a problem with edge lift, and a lack of adhesive hold, as demonstrated by the fact that only 26 of the 40 samples applied to the backs of volunteers remained at the end of the test period. Furthermore, the RESTORE™, TEGASORB™, and DUODERM EXTRA-THIN™ products display significant skin residue problems after a prolonged period of application. Only the wound dressings of the present invention provide the combined advantages of high absorbency and wet integrity with good skin adhesion both wet and dry, minimal edge lift, and low to no skin residue.

Examples 30–32, and Comparative Example 33

Three adhesive compositions of the present invention were tested for potential use as ostomy and/or prosthesis adhesives by measuring their shear holding power in minutes/500 g. The specific compositions of the adhesives of Examples 30–32 are shown in Table 5. All of these compositions were formed by the same procedures as used in Examples 1–13. In addition, the same non-irradiated composition as that of Example 30 (Comparative Example 33) was tested. Furthermore, two commercially available ostomy adhesives were also tested: DUROADHESIVE™ (a product of Convatec; Squibb and Sons, Inc., Princeton, N.J.; believed to be a KRATON™-based composition under U.S. Pat. No. 4,551,490), and Hollister's Ostomy Skin Barrier Adhesive (a product of Hollister, Inc., Libertyville, Ill.; believed to be an EVA-based composition under U.S. Pat. Nos. 4,477,325 and 4,738,257). The shear holding power in minutes/500 grams for the adhesive compositions of Examples 30–32, Comparative Example 33, DUROADHESIVE™, and the Hollister Ostomy Skin Barrier Adhesive are shown in Table 6.

TABLE 5

Specific composition of Example adhesives 30–32.

| Ex. No. | LM-MH (PIB) | Polyisoprene | CMC | X-link CMC | CARBOPOL (PAA) | Min. Oil |
|---|---|---|---|---|---|---|
| 30 | 30 | 40 | 12.5 | 10 | 7.5 | — |
| 31 | 37.5 | 40 | 10 | 5 | 6.25 | 1.25 |
| 32 | 45 | 40 | — | 5 | 10 | — |

TABLE 6

Shear holding power (minutes/500 g) for the adhesive compositions of Examples 30–32, Comparative Example 33, DUROADHESIVE ™, and the Hollister Ostomy Skin Barrier Adhesive.

| Sample Composition | Shear Holding Power (minutes/500 g) |
|---|---|
| Example 30 | 8700+ |
| Example 31 | 1276 |
| Example 32 | 1012 |
| Comparative Example 33 | 56 |
| DUROADHESIVE ™ | 233 |
| Hollister Adhesive | 52 |

The data of Table 6 show that the adhesive compositions of the present invention exhibit superior shear holding power, a necessary property for an effective ostomy and/or prosthesis adhesive, in comparison to non-irradiated compositions, as well as currently available products. In addition, these compositions are formulated with low relative absorbency. Thus, the composition of Example 31 exhibits an absorbency of 12% after 24 hours of exposure to aqueous fluids.

Examples 34–35

Two adhesive compositions according to the present invention were formed from the same materials and according to the same procedures as Examples 1–13, except that WINGTACK™ 95 (Goodyear Chemical Co., Akron, Ohio), a commercially available synthetic polyterpene tackifier was added as an additional component. These compositions were formed into wound dressings according to the same procedures as for Examples 1–13, and were tested for percent absorbency and percent wet integrity according to the procedures previously described. The specific composition, percent absorbency, and percent wet integrity for the wound dressings of Examples 34–35 are shown in Table 7. The data of Table 7 show that even with the inclusion of non-elastic tackifiers, the adhesive compositions of the present invention maintain their advantages of high absorbency combined with high wet integrity.

TABLE 7

Specific composition, percent absorbency, and percent wet integrity for the wound dressings of Examples 34–35.

| Ex | LM-MH (PIB) | Poly-iso-prene | CMC | X-link CMC | Wing-tack 95 | Absorb. (%) | Wet Integ. (%) |
|---|---|---|---|---|---|---|---|
| 35 | 20 | 40 | 20 | 15 | 7.5 | 157 | 89 |
| 36 | 15 | 40 | 20 | 15 | 6 | 300 | 81 |

While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A pressure sensitive hydrocolloid adhesive composition consisting essentially of i) about 20–50 percent by weight of a hydrophobic, unsaturated, elastomeric homopolymer, ii) about 20–60 percent by weight of a tackifier selected from the group consisting of polyisobutylene, synthetic polyterpene tackifiers and combinations thereof and iii) about 5–60 percent by weight of a hydrocolloid absorbent selected from the group consisting of a natural hydrocolloid, a semi-synthetic hydrocolloid, a synthetic hydrocolloid, and combinations thereof, wherein the homopolymer is cross-linked by 5–200 kGy gamma radiation to provide the composition with a cross-linked matrix having a wet integrity value of at least about eighty percent, a shear hold value of at least 500 min/500 g and a dry cohesive strength which prevents adhesive composition breakage or delamination when a 1×6 cm strip of the adhesive composition is slowly peeled off a polyester adhesive tape at a 90 degree angle and at a speed of 10 mm/minute.

2. An adhesive composition of claim 1, wherein the hydrophobic, unsaturated, elastomeric homopolymer has at least about 50 mole percent unsaturation.

3. An adhesive composition of claim 1, wherein the hydrophobic, unsaturated, elastomeric homopolymer has at least about 90 mole percent unsaturation.

4. An adhesive composition of claim 1, wherein the hydrophobic, unsaturated, elastomeric homopolymer is selected from the group consisting of a straight-chain unsaturated aliphatic homopolymer, a branched unsaturated aliphatic homopolymer, and combinations thereof.

5. An adhesive composition of claim 4, wherein the elastomeric homopolymer is selected from the group consisting of polyisoprene, polybutadiene, and combinations thereof.

6. An adhesive composition of claim 1, wherein the tackifier comprises a nonelastomeric synthetic polyterpene tackifier.

7. An adhesive composition of claim 1, wherein the hydrocolloid absorbent is selected from the group consisting of pectin, gelatin, a carboxymethylcellulose salt, a cross-linked carboxymethylcellulose salt, cross-linked polyacrylic acid, and combinations thereof.

8. An adhesive composition of claim 1 containing about 0.5 percent to 10 percent by weight of a plasticizer component.

9. An adhesive composition of claim 1, wherein the adhesive composition exhibits a wet integrity value of at least about ninety percent.

10. A wound dressing comprising the adhesive composition of claim 1 coated on a surface of a moisture vapor permeable backing.

11. A wound dressing of claim 10, wherein the backing further comprises a release coating coated on the surface of the backing opposite the surface coated with the adhesive composition.

12. A wound dressing of claim 10, wherein the backing is a transparent film of polyurethane or porous polyethylene.

13. A wound dressing of claim 10, wherein the backing extends beyond the periphery of the adhesive coating on all sides, and wherein at least a portion of the extended backing surface is coated with a second pressure sensitive adhesive.

14. A method of treating a wound comprising applying to the wound the composition of claim 1.

15. A method of forming a pressure sensitive adhesive composition comprising:

(a) compounding a mixture of i) about 20–50 percent by weight of a hydrophobic, unsaturated, elastomeric homopolymer, ii) about 20–60 percent by weight of a tackifier selected from the group consisting of polyisobutylene, synthetic polyterpene tackifiers and combinations thereof and iii) about 5–60 percent by weight of a hydrocolloid absorbent selected from the group consisting of a natural hydrocolloid, a semi-synthetic hydrocolloid, a synthetic hydrocolloid, and combinations thereof to form a hydrocolloid adhesive mass; and (b) irradiating the hydrocolloid adhesive mass with a dose of radiation of from about 5 kGy to 200 kGy.

16. A method of forming an adhesive composition of claim 15, further comprising, adding a plasticizer to the mixture.

17. A method of forming an adhesive composition of claim 15, further comprising adhering the adhesive sheet to a least a portion of one major surface of a moisture vapor permeable backing.

* * * * *

UNITED STATES PATENT AND TRADEMARK OFFICE
CERTIFICATE OF CORRECTION

PATENT NO.: 5,633,010
DATED: May 27, 1997
INVENTOR(S): Yen-Lane Chen

It is certified that error appears in the above-identified patent and that said Letters Patent is hereby corrected as shown below:

In the title page, under FOREIGN PATENT DOCUMENTS at Pat. No. 91/19480 dated 12/1991, please delete "European Pat. Off." and insert in place thereof --WIPO--.

In the title page, under FOREIGN PATENT DOCUMENTS at Pat. No. 0272149 dated 3/1992, please delete "WIPO" and insert in place thereof --European Pat. Off.--.

Col. 2, line 26: Please delete the article "a" after the word "provides" and insert in place thereof --an--.

Col. 4, line 8: Between the words "to" and "exposed" please insert the word --be--.

Col. 4, line 60: Please delete the word "in" and insert in place thereof --is--.

Col. 4, line 61: Please delete the word "composition" and insert in place thereof --compositions--.

Col. 9, line 20: Please delete the article "an" and insert in place thereof --a--.

Col. 9, line 41: Please delete the article "an" and insert in place thereof --a--.

Claim 17, col. 18, line 56: Before the word "least," please delete the article "a" and insert in place thereof --at--.

Signed and Sealed this

Seventeenth Day of April, 2001

*Attest:*

NICHOLAS P. GODICI

*Attesting Officer*     Acting Director of the United States Patent and Trademark Office